United States Patent [19]

Maruyama et al.

[11] 3,953,433

[45] Apr. 27, 1976

[54] SENSITIZER FOR USE IN ELECTROPHOTOGRAPHIC LIGHT-SENSITIVE MATERIAL

[75] Inventors: Shoji Maruyama, Sagamihara; Tomio Kubota; Katue Kojima, both of Tokyo; Hiroshi Tamura, Kawasaki; Masahide Harada, Tokyo, all of Japan

[73] Assignee: Ricoh Co., Ltd., Tokyo, Japan

[22] Filed: Jan. 3, 1974

[21] Appl. No.: 430,587

Related U.S. Application Data

[63] Continuation-in-part of Ser. No. 259,558, June 5, 1972, abandoned.

[30] Foreign Application Priority Data

June 22, 1971 Japan ................................ 46-45063

[52] U.S. Cl. ................................ 260/240 D; 96/1.6; 260/240 R; 260/240 E

[51] Int. Cl.$^2$ .................... C07D 311/04; G03G 5/06

[58] Field of Search ........ 260/240 R, 240 D, 240 E; 96/1.6

[56] References Cited

UNITED STATES PATENTS

| | | | |
|---|---|---|---|
| 3,526,502 | 9/1970 | Murakami et al. | 96/1.5 |
| 3,617,268 | 11/1971 | Murakami et al. | 96/1.5 |
| 3,712,811 | 1/1973 | Murakami et al. | 96/1.6 |

*Primary Examiner*—Arthur P. Demers
*Attorney, Agent, or Firm*—Cooper, Dunham, Clark, Griffin & Moran

[57] ABSTRACT

There are provided sensitizers for electrophotographic light-sensitive materials including organic photoconductors and electrophotographic light-sensitive materials containing same. The sensitizers are reaction products comprising benzopyrylium salt and benzopyran.

24 Claims, 13 Drawing Figures

SENSITIZER FOR USE IN ELECTROPHOTOGRAPHIC LIGHT-SENSITIVE MATERIAL

RELATED APPLICATIONS

Figure 1:
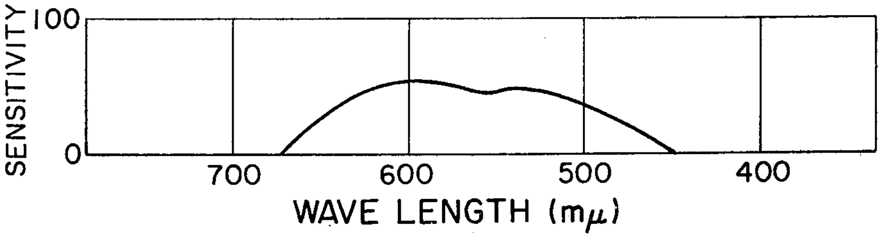

This application is a continuation-in-part of copending application Ser. No. 259,558 filed June 5, 1972, and now abandoned.

BACKGROUND OF THE INVENTION

It is well known to use organic photoconductors such as polyvinylcarbazole instead of inorganic photoconductors such as photoconductive zinc oxide or selenium in electrophotographic light-sensitive materials. However, with organic photoconductors the sensitivity is low compared with the inorganic photoconductors. Accordingly, in order to improve the sensitivity of organic photoconductors, it has been proposed to add certain coloring material for sensitization. In such manner, the sensitivity of the organic photoconductors may be improved to a degree that it can be used in a practical manner. There is however still need for improvement.

It is an object of the present invention to provide sensitizers which will impart high sensitivity to organic photoconductors.

SUMMARY OF THE INVENTION

The present invention relates to sensitizers for electrophotographic light-sensitive materials including organic photoconductors and electrophotographic light-sensitive materials containing said sensitizers.

The sensitizers of the present invention are reaction products comprising benzopyrylium salt having the following general formulas (I) and (II) and benzopyran having the following general formulas (I′) and (II′).

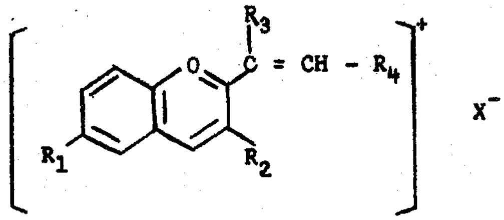

..... (I)

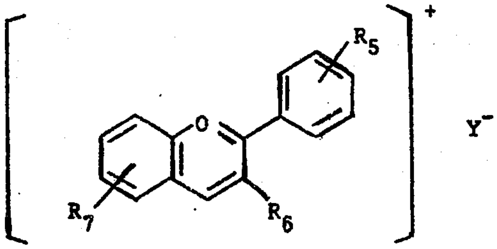

..... (II)

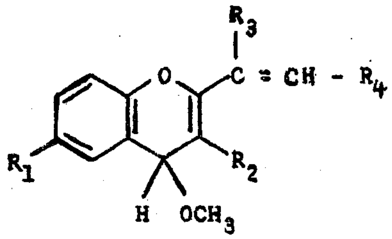

..... (I′)

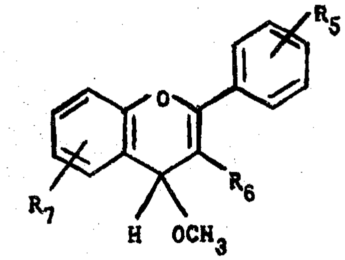

..... (II′)

wherein $R_1$ is a halogen atom, or a methyl, ethyl, alkoxyl, nitro or cyano group; $R_2$ and $R_6$ are a hydrogen atom, or a methyl, ethyl, phenyl or alkoxyphenyl group; $R_3$ is a hydrogen atom or an alkyl group of $C_1$ to $C_4$; and $R_4$ is a phenyl group, or phenyl group substituted by a halo, methyl, ethyl, carboxyl, alkoxyl, nitro or cyano substituent; $R_5$ is a hydrogen or halogen atom, or a methyl, methoxyl, nitro or amino group; $R_7$ is a hydrogen or halogen atom, or a methyl, ethyl, alkoxyl, nitro or cyano group; and $X^-$ and $Y^-$ are $Cl^-$, $Br^-$, $I^-$, $ClO_4^-$, $IO_4^-$ or $BF_4^-$.

The compounds of formulas (I), (II), (I') and (II') may be prepared by known methods.

1. Benzopyrylium salts (I) may be prepared by condensing an appropriately substituted 2-hydroxybenzaldehyde with acetophenone derivatives in an acidic solvent in the presence of a mineral acid at room temperature and then carrying out a cyclic condensation with an appropriate aldehyde.
2. Benzopyrylium salts (II) may be prepared by condensing an appropriately substituted 2-hydroxybenzaldehyde with an appropriately substituted acetophenone in an acidic solvent in the presence of a mineral acid at room temperature.
3. A desired anion may be introduced to benzopyrylium salts, for example, by effecting the condesation reaction in the presence of an acid or salt having the desired anion or by effecting a subsequent anion-exchange.
4. Benzopyrans (I') and (II') may be prepared, for example, by refluxing benzopyrylium salts of formulas (I) and (II) respectively with an alkali in a mixture of methyl alcohol and benzene.

The reaction products according to the present invention comprises 1 part by weight of benzopyrylium salt and 0.5 to 2 parts by weight of benzopyran.

The following Preparations and Examples are given by way of illustration only;

Preparation 1

2-(p-methoxystyryl)-3-phenyl-6-chlorobenzopyrylium perchlorate (the following formula 4)

12 g of 2-hydroxy-5-chlorobenzaldehyde (the above formula 1) and 11 g of benzyl methyl ketone (the above formula 2) were dissolved in 45 ml of 95% formic acid and to this solution was dropwise with stirring, added 30 ml of 35% hydrochloric acid, at room temperature, over 20 to 30 minutes.

Stirring was continued for about 2 hours. To this solution were added a solution of 12 g of anisaldehyde in 50 ml of 90% formic acid and thereafter dropwise with stirring, 10 ml of 35% hydrochloric acid at room temperature over 20 minutes. Stirring was continued for about one hour and the solution was allowed to stand overnight. The solution was added dropwise with stirring over about 2 hours to 100 ml of an aqueous solution containing 15% perchloric acid, cooled below 10° C. A crude crystalline product separated from the solution. The crude product was filtered off and washed several times with ethyl ether. After recrystallisation from acetic acid, the crude crystalline product yielded 15 g of the title compound (m.p. 214° to 216° C).

| Analysis: | C(%) | H(%) | Cl(%) |
|---|---|---|---|
| Calculated (for $C_{24}H_{18}Cl_2O_6$) | 80.90 | 3.83 | 14.98 |
| Found | 60.63 | 3.77 | 14.64 |

This compound showed an absorption maximum (λmax) at a wave length of 577 mμ and molecular extinction coefficient (ε) of $6.51 \times 10^4$.

Preparation 2

2-(p-methoxystyryl)-3-phenyl-4-methoxy-6-chloro-1,4-benzopyran (the following formula 5)

(5)

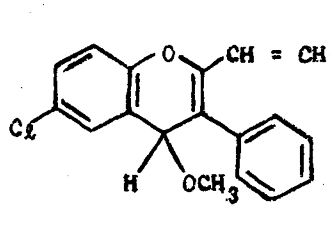

(1) (2) (3) (4)

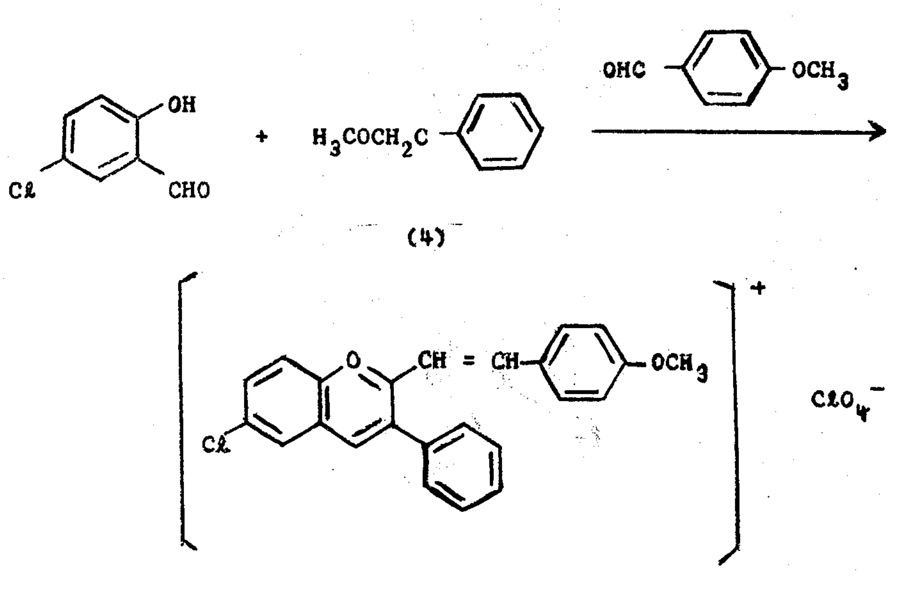

10 g of 2-(p-methoxystyryl)-3-phenyl-6-chlorobenzopyrylium perchlorate (the above formula 4) and 15 g of sodium bicarbonate were dissolved in a mixture of 50 ml of methyl alcohol and 100 ml of benzene and this solution was heated for about 1 hour. During heating, the color of the solution changed from purple to yellow. After cooling, the solution was filtered and the filtrate was reduced in volume under reduced pressure. The residue was dissolved in methyl alcohol. On pouring the resulting solution into ice-water, a light yellowish crystalline product separated. After having been filtered off and washed with water and then dried under vacuum, the product yielded quantitatively the title compound (m.p. 74° to 76° C) in the form of crystals.

| Analysis | C(%) | H(%) | Cl(%) |
|---|---|---|---|
| Calculated (for $C_{25}H_{21}ClO_3$) | 74.41 | 5.19 | 8.78 |
| Found | 74.56 | 5.32 | 8.50 |

This compound showed an absorption maximum (λmax) at a wave length of 420 mμ and molecular extinction coefficient (ε) of 3,47 × $10^4$.

Preparation 3

2-phenylbenzopyrylium perchlorate (the following compound 8)

(6) (7) (8)

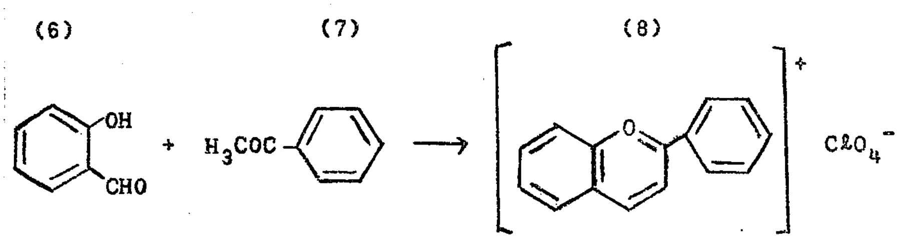

50 g 2-hydroxybenzaldehyde (the above formula 6) and 50 g of acetophenone (the above formula 7) were dissolved in 180 ml of 90% formic acid and to this solution was added 60 ml of 60% aqueous solution of perchloric acid, and then an excess of hydrogen chloride gas was bubbled in. The resulting solution was allowed to stand overnight. A crude crystalline product separated on pouring the solution dropwise over a period of about 30 minutes into 500 ml of cooled ethyl ether with stirring. The crude product was filtered off and washed several times with ethyl ether. After recrystallisation from acetic acid, the crude product gave 60 g of the title compound (m.p. 176° to 178° C) as crystals.

| Analysis: | C(%) | H(%) | Cl(%) |
|---|---|---|---|
| Calculated (for $C_{15}H_{11}ClO_5$) | 58.70 | 3.60 | 11.58 |
| Found | 58.53 | 3.51 | 11.43 |

This compound showed an absorption maximum (λmax) at a wave length of 410 mμ and molecular extinction coefficient (ε) of 3.68 × $10^4$.

Preparation 4

2-phenyl-4-methoxy-1,4-benzopyran (the following formula 9)

(9)

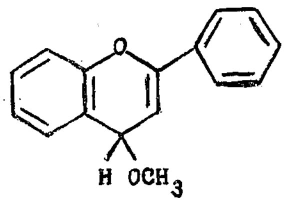

7.1 g of 2-phenylbenzopyrylium perchlorate (the above formula 8) and 15 g of sodium bicarbonate were dissolved in a mixture of 50 ml of methyl alcohol and 100 ml of benzene and this solution was heated for about 1 hour. After cooling, the solution was filtered and the filtrate was evaporated under reduced pressure. The residue was dissolved in benzene. This benzene solution was washed with water in a separating funnel to remove inorganic substances present in the benzene solution. The benzene solution was dried overnight over sodium sulfate. The benzene solution was then filtered to remove sodium sulfate. The title compound (m.p. 128° to 130° C) was obtained as a glass in quantitative yield on removing benzene.

| Analysis: | C(%) | H(%) |
|---|---|---|
| Calculated (for $C_{16}H_{14}O_2$) | 80.87 | 5.88 |
| Found | 80.31 | 5.52 |

This compound showed an absorption maximum at a wave length of 303 mμ and molecular extinction coefficient (ε) of 1.14 x $10^{-4}$.

Benzopyrylium salts obtained in Preparations 1 and are perchlorates having $ClO_4^-$ as an anion. Benzopyrylium salts having another anion such as $Cl^-$, $Br^-$, $I^-$, $IO_4^-$ or $BF_4^-$ can be prepared using an acid or a salt having the desired anion, instead of perchloric acid.

We have found that reaction product prepared by combination of benzopyrylium salt (I) and benzopyran (II') or combination of benzopyrylium salt (II) and benzopyran (I') is surprisingly effective as a sensitizer for organic photoconductors. The present invention is based on this discovery.

Reaction products comprising benzopyrylium salt (I) or (II) and benzopyran (I') or (II') were prepared as shown in the Examples 1 to 22. The reaction products are not limited to those as shown in the examples.

The reaction products as shown in Examples 2 to 22 were prepared analogously to the method of Example 1.

EXAMPLE 1

Reaction product No. 1 comprising 2-phenylbenzopyrylium perchlorate (II) and 2-(p-methoxystyryl)-3-phenyl-4-methoxy-6-chloro-1,4-benzopyran (I')

Preparation of Reaction product No. 1

6 g of 2-phenylbenzopyrylium perchlorate (obtained in Preparation 3) and 10 g of 2-(p-methoxystyryl)-3-phenyl-4-methoxy-6-chloro-1,4-benzopyran (obtained in Preparation 2) were dissolved in 600 ml of dichloroethane. This solution was heated at a temperature of 50° to 60° C for 5 hours under reflux and then evaporated under reduced pressure until the solution was reduced at 150 ml. After having been cooled to ambient temperature, the solution was poured dropwise into 600 ml of ethyl ether to separate a crystalline product. After allowing to stand for about 30 minutes, the product was filtered off. The product obtained was dissolved in dichloroethane. On dropwise pouring of this solution into ethyl ether and subsequent filtering of the crystalline product followed by drying under vacuum, 5.2 g of the title reactions product (m.p. 114° to 116° C) was obtained in the form of crystals.

EXAMPLE 2

Reaction product No. 2 comprising 2-phenylbenzopyrylium perchlorate (II) and 2-(p-methoxystyryl)-3-phenyl-4,6-dimethoxy-1,4-benzopyran (I')

EXAMPLE 3

Reaction product No. 3 comprising 2-phenylbenzopyrylium perchlorate (II) and 2-(p-methoxystyryl)-3-phenyl-4-methoxy-6-methyl-1,4-benzopyran (I')

EXAMPLE 4

Reaction product No. 4 comprising 2-(p-nitrophenyl)-benzopyrylium perchlorate (II) and 2-(p-methoxystyryl)-3-phenyl-4,6-dimethoxy-1,4-benzopyran (I')

EXAMPLE 5

Reaction product No. 5 comprising 2-(p-chlorophenyl)-benzopyrylium perchlorate (II) and 2-(p-methoxystyryl)-3-phenyl-4,6-dimethoxy-1,4-benzopyran (I')

EXAMPLE 6

Reaction product No. 6 comprising 2-(p-nitrophenyl)-6-methoxybenzopyrylium perchlorate (II) and 2-(p-methoxystyryl)-3-phenyl-4,6-dimethoxy-1,4-benzopyran (I')

EXAMPLE 7

Reaction product No. 7 comprising 2-(p-chlorophenyl)-6-methoxybenzopyrylium perchlorate (II) and 2-(p-methoxystyryl)-3-phenyl-4,6-dimethoxy-1,4-benzopyran (I')

EXAMPLE 8

Reaction product No. 8 comprising 2-(p-chlorophenyl)-6-methoxybenzopyrylium perchlorate (II) and 2-(p-methoxystyryl)-3-phenyl-4-methoxy-6-methyl-1,4-benzopyran (I')

EXAMPLE 9

Reaction product No. 9 comprising 2-(p-aminophenyl)-benzopyrylium perchlorate (II) and 2-(p-methoxystyryl)-3-phenyl-4,6-dimethoxy-1,4-benzopyran (I')

EXAMPLE 10

Reaction product No. 10 comprising 2-(p-methylphenyl)-benzopyrylium perchlorate (II) and 2-(p-methoxystyryl)-3-phenyl-4,6-dimethoxy-1,4-benzopyran (I')

EXAMPLE 11

Reaction product No. 11 comprising 2-(p-methoxyphenyl)-benzopyrylium perchlorate (II) and 2-(p-methoxystyryl)-3-phenyl-4,6-dimethoxy-1,4-benzopyran (I')

EXAMPLE 12

Reaction product No. 12 comprising 2-(p-methoxystyryl)-3-phenyl-6-chlorobenzopyrylium perchlorate (I) and 2-phenyl-4-methoxy-1,4-benzopyran (II')

EXAMPLE 13

Reaction product No. 13 comprising 2-(p-methoxystyryl)-3-phenyl-6-methoxybenzopyrylium perchlorate (I) and 2-phenyl-4-methoxy-1,4-benzopyran (II')

EXAMPLE 14

Reaction product No. 14 comprising 2-phenyl-6-methoxybenzopyrylium perchlorate (II) and 2-(α-isopropyl-carboxystyryl)-4-methoxy-6-methyl-1,4-benzopyran (I')

EXAMPLE 15

Reaction product No. 15 comprising 2-p-methoxyphenyl-6-methylbenzopyrylium perchlorate (II) and 2-p-cyanostyryl-3-phenyl-4-methoxy-6-chloro-1,4-benzopyran (I')

EXAMPLE 16

Reaction product No. 16 comprising 2-phenyl-6-chlorobenzopyrylium perchlorate (II) and 2-(2,4-dichlorostyryl)-3-phenyl-4-methoxy-6-nitro-1,4-benzopyran (I')

EXAMPLE 17

Reaction product No. 17 comprising 2-p-nitrophenylbenzopyrylium perchlorate (II) and 2-p-methylstyryl-3-phenyl-4-methoxy-6-ethyl-1,4-benzopyran (I')

EXAMPLE 18

Reaction product No. 18 comprising 2-p-cyanostyryl-3-phenyl-6-chlorobenzopyrylium perchlorate (I) and 2-p-methoxyphenyl-4-methoxy-6-methyl-1,4-benzopyran (II')

EXAMPLE 19

Reaction product No. 19 comprising 2-(2,4-dichlorostyryl)-3-phenyl-6-nitrobenzopyrylium perchlorate (I) and 2-p-methylphenyl-4-methoxy-6-chloro-1,4-benzopyran (II')

EXAMPLE 20

Reaction product No. 20 comprising 2-(α-isopropyl-p-carboxystyryl)-6-methylbenzopyrylium perchlorate (I) and 2-p-chlorophenyl-4,5-dimethoxy-1,4-benzopyran (II')

EXAMPLE 21

Reaction product No. 21 comprising 2-p-nitrostyryl-3-phenyl-6-benzopyrylium perchlorate (I) and 2-p-aminophenyl-4-methoxy-1,4-benzopyran (II')

EXAMPLE 22

Reaction product No. 22 comprising 2-p-methoxystyryl-3-phenyl-6-chlorobenzopyrylium perchlorate (I) and 2-p-nitrophenyl-4-methoxy-1,4-benzopyran (II')

Figure 2:
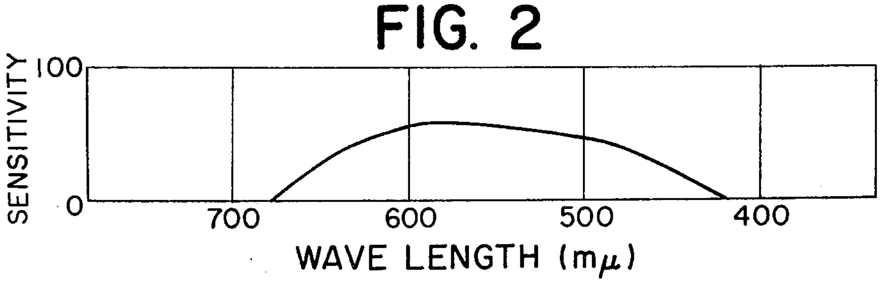
Figure 3:
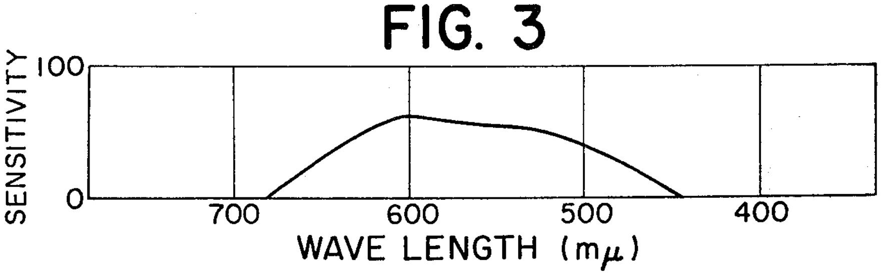
Figure 4:
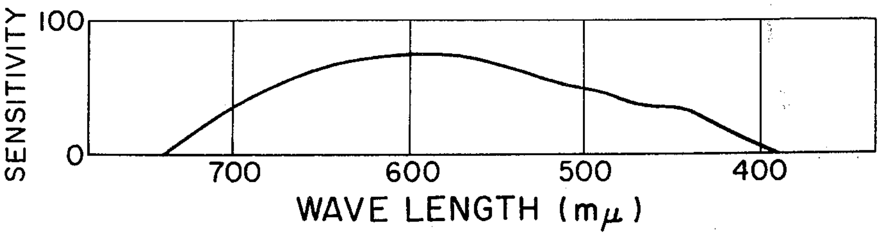
Figure 5:
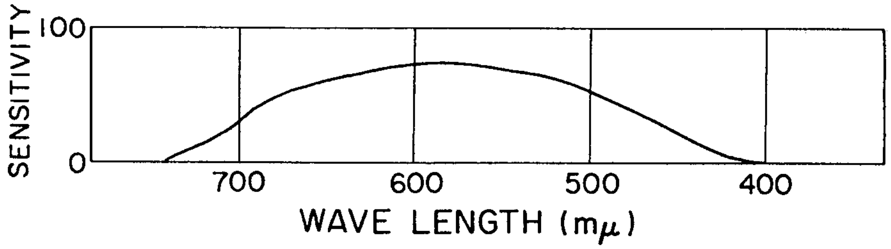
Figure 6:
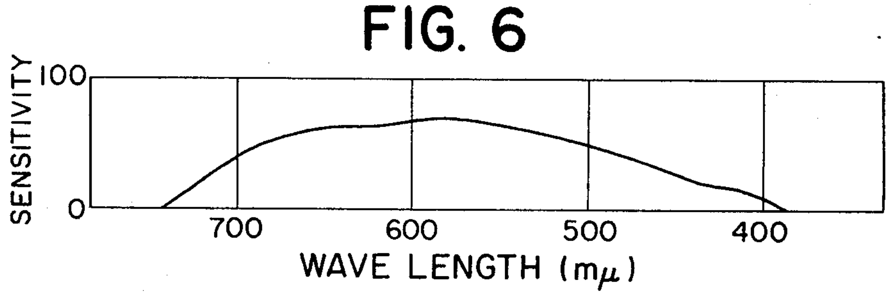
Figure 7:
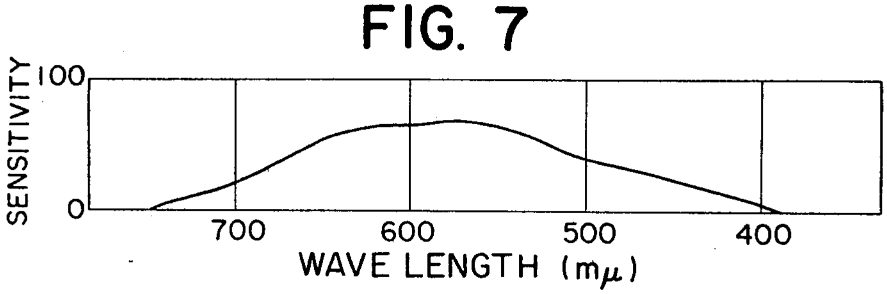
Figure 8:
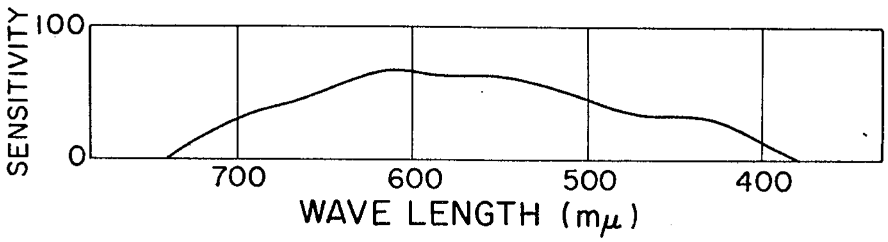
Figure 9:
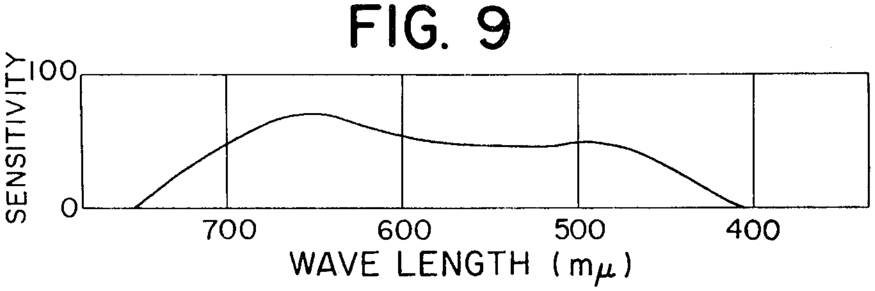
Figure 10:
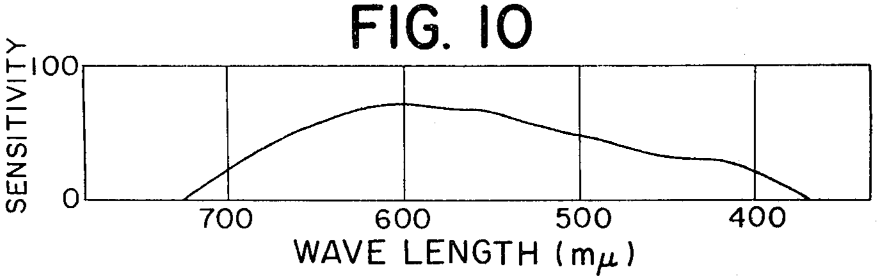
Figure 11:
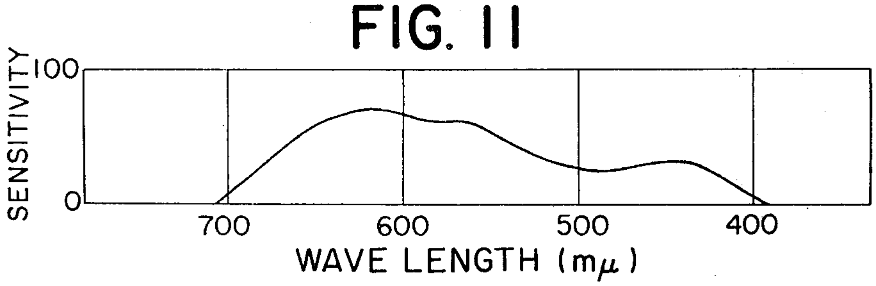
Figure 12:
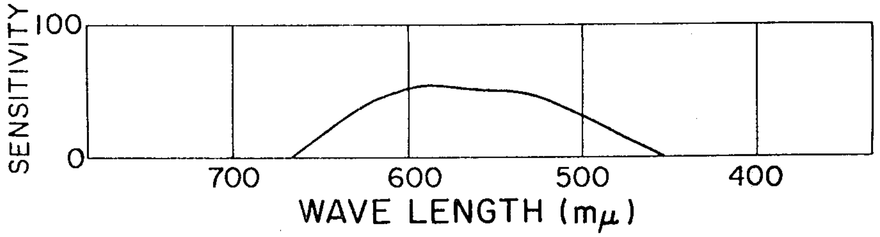
Figure 13:
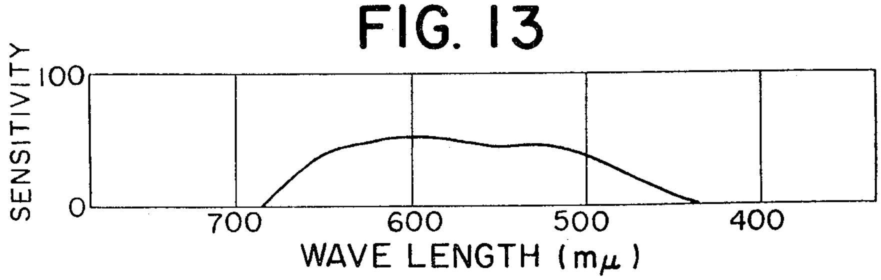

Absorption maxima (λmax) and specific extinction coefficient (ε) of the reaction products Nos. 1 to 22 in dichloroethane are shown in the following Table-1 and the spectral sensitivity curves of the reaction products Nos. 1 to 13 are shown in FIG. 1 to FIG. 13 respectively of the accompanying drawings.

Table - 1

| Reaction product | Color of solution | Wave length of absorption maximum ($\lambda_{max}$) (mμ) | Specific extinction coefficient (ε; $1 \times 10^4$) |
|---|---|---|---|
| 1 | Purple | 582 | 7.08 |
| 2 | " | 582 | 8.78 |
| 3 | " | 588 | 13.78 |
| 4 | " | 580 | 7.19 |
| 5 | " | 579 | 6.33 |
| 6 | " | 580 | 6.04 |
| 7 | " | 577 | 4.76 |
| 8 | " | 590 | 4.45 |
| 9 | Blue | 635 | 4.52 |
| 10 | Purple | 584 | 4.17 |
| 11 | Royal purple | 608 | 8.33 |
| 12 | Purple | 582 | 4.83 |
| 13 | " | 580 | 5.25 |
| 14 | " | 568 | 7.75 |
| 15 | " | 580 | 7.33 |
| 16 | " | 580 | 6.31 |
| 17 | " | 581 | 7.01 |
| 18 | Blue | 623 | 5.16 |
| 19 | Purple | 578 | 4.96 |
| 20 | " | 581 | 6.52 |
| 21 | " | 580 | 5.21 |
| 22 | " | 579 | 6.00 |

The reaction products according to the present invention are used as sensitizers for organic photoconductors in an amount of from 0.1 to 2.0% by weight based on the amount of organic photoconductors.

The organic photoconductors include polyvinylcarbazole and its derivatives such as alkylated-or halogenated polyvinylcarbazole, polyvinylanthracene, diphenylamine, diphenylpyrrole, triazole, benzothiazole and benzoxazole.

Electrophotographic light-sensitive materials containing the reaction products according to the invention are generally sensitive to light of long wavelength, i.e., visible light, so that reddish patterns, or figures in an original can be reproduced by the electrophotographic light-sensitive material.

The sensitizing properties of the reaction products according to the invention are illustrated by the following example.

| Example | |
|---|---|
| Solution of brominated polyvinylcarbazole in chlorobenzene (6.7%) | 350 g |
| Solution of polycarbonate in dichloroethane (10%) | 70 g |
| Diphenyl chloride (sold by Kanegafuchi Chemical Industries Co., Ltd. under a trade mark of "KANECHLOR") | 4.7 g |

To separate samples of a mixture of these ingredients were added solutions of 120 mg of each of the reaction products Nos. 1 to 13 in a small amount of dichloroethane. The light-sensitive solutions obtained were each applied to a paper surface to give electrophotographic light-sensitive materials. The light-sensitive layer on each had a thickness of about 5μ.

The color sensitivity, the peak of the light-sensitive range and the photographic sensitivity of each light-sensitive material were measured as follows:

i. Measurement of color sensitivity

Using an electrophotographic printing machine sold by K. K. Ricoh under the trade mark "RICOH ELECTRONIC PRINTER BS-2," the electrophotographic light-sensitive materials were negatively charged by a corona discharge, exposed to light through an original having black and reddish patterns and developed by contact with a positively charged resinous toner powder.

$$\text{Color sensitivity} = \frac{\text{Image density obtained by the reddish pattern}}{\text{Image density obtained by the black pattern}} \times 100$$

ii. Measurement of the peak of the light-sensitive range

Each light-sensitive material was negatively charged by a corona discharge of 6 kV, exposed to light for 10 seconds using a slit width of 2 mm in a spectrograph and then developed by the same method described above. Using the spectrographic print obtained, the peak of the light-sensitive range could be measured.

iii. Measurement of photographic sensitivity

Each light-sensitive material was negatively charged by a corona discharge of about 6 kV. Using this charged light-sensitive material the exposure required to reduce the surface electric potential to one half (E½ lux·sec) or one fifth (E1/5 lux·sec) of its original value were measured using a tungsten incandescent lamp and a rotary sector type electrometer.

The color sensitivity, the peak of the photosensitive ranges and the photographic sensitivities (E½ and E1/5) obtained, are shown in the Table-2:

Table - 2

| Reaction product No. | Color sensitivity (%) | Peak of light-sensitive range (mμ) | E1/2 (lux.sec) | E1/5 (lux.sec) |
|---|---|---|---|---|
| 1 | 39.3 | 594 | 54.0 | 136.0 |
| 2 | 50.0 | 580 | 31.0 | 79.0 |
| 3 | 51.1 | 604 | 28.5 | 73.5 |
| 4 | 67.8 | 586 | 18.5 | 48.5 |
| 5 | 80.5 | 584 | 19.0 | 50.0 |

Table - 2-continued

| Reaction product No. | Color sensitivity (%) | Peak of light-sensitive range (mμ) | E1/2 (lux.sec) | E1/5 (lux.sec) |
|---|---|---|---|---|
| 6 | 76.0 | 585 | 25.0 | 66.5 |
| 7 | 67.0 | 587 | 19.0 | 51.0 |
| 8 | 76.3 | 608 | 17.5 | 46.5 |
| 9 | 56.0 | 662 | 26.5 | 70.0 |
| 10 | 78.7 | 616 | 19.0 | 50.0 |
| 11 | 77.1 | 628 | 24.8 | 71.9 |
| 12 | 79.4 | 595 | 53.5 | 193.0 |
| 13 | 50.0 | 580 | 43.5 | 106.0 |

The electrophotographic light-sensitive materials containing these reaction products according to the present invention showed superior color sensitivity and a better reproduction of reddish patters on an original than electrophotographic light-sensitive materials containing only benzopyrylium salts as a sensitizer.

We claim:

1. A sensitizer for an electrophotographic light-sensitive material including an organic photoconductor, which is a reaction product comprising 1 part by weight of a benzopyrylium salt having the following general formula (I):

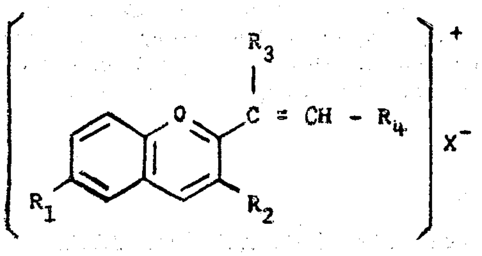

(I)

wherein $R_1$ is a halogen atom, or a methyl, ethyl, alkoxyl, nitro or cyano group; $R_2$ is a hydrogen atom, or a methyl, ethyl, phenyl or alkoxyphenyl group; $R_3$ is a hydrogen atom or an alkyl group of $C_1$ to $C_4$; $R_4$ is a phenyl group, or a phenyl group substituted by a halo, methyl, ethyl, carboxyl, alkoxyl, nitro or cyano substituent; and $X^-$ is $Cl^-$, $Br^-$, $I^-$, $CAO_4^-$, $IO_4^-$ or $BF_4^-$, and from 0.5 to 2 parts by weight of a benzopyran having the following general formula (II'):

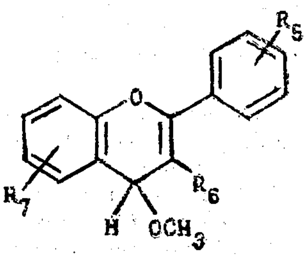

(II')

wherein $R_5$ is a hydrogen or halogen atom, or a methyl, methoxyl, nitro or amino group; $R_6$ is same as $R_2$ of the general formula (I); $R_7$ is a hydrogen or halogen atom, or a methyl, ethyl, alkoxyl, nitro or cyano group.

2. A sensitizer for an electrophotographic light-sensitive material including an organic photoconductor, which is a reaction product comprising 1 part by weight of a benzopyrylium salt having the following general formula (II):

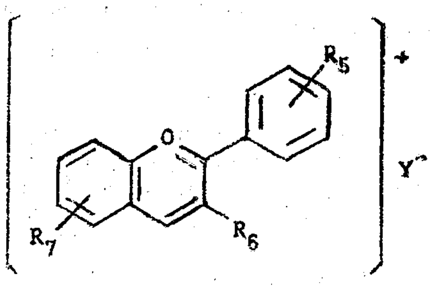

(II)

wherein $R_5$ is a hydrogen or halogen atom, or a methyl, methoxyl, nitro or amino group; $R_6$ is a hydrogen atom, or a methyl, ethyl, phenyl or alkoxyphenyl group; $R_7$ is a hydrogen or halogen atom, or a methyl, ethyl, alkoxyl, nitro or cyano group; $Y^-$ is $Cl^-$, $Br^-$, $I^-$, $ClO_4^-$, $IO_4^-$ or $BF_4^-$, and from 0.5 to 2 parts by weight of a benzopyran having the following general formula (I'):

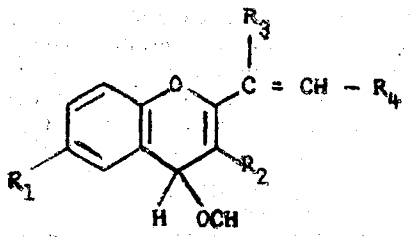

wherein $R_1$ is a halogen atom, or a methyl, ethyl, alkoxyl, nitro or cyano group; $R_2$ is same as $R_6$ of the general formula (II); $R_3$ is a hydrogen atom or an alkyl group of $C_1$ to $C_4$; $R_4$ is a phenyl group, or a phenyl group substituted by a halo, methyl, ethyl, carboxyl, alkoxyl, nitro or cyano substituent.

3. A sensitizer according to claim 1 wherein said benzopyrylium salt is 2-(p-methoxystyryl)-3-phenyl-6-chlorobenzopyrylium perchlorate and said benzopyran is 2-phenyl-4-methoxy-1,4-benzopyran.

4. A sensitizer according to claim 1 wherein said benzopyrylium salt is 2-(p-methoxystyryl)-3-phenyl-6-methoxybenzopyrylium perchlorate and said benzopyran is 2-phenyl-4-methoxy-1,4-benzopyran.

5. A sensitizer according to claim 2, wherein said benzopyrylium salt is 2-phenylbenzopyrylium perchlorate and said benzopyran is 2-(p-methoxystyryl)-3-phenyl-4-methoxy-6-chloro-1,4-benzopyran.

6. A sensitizer according to claim 2 wherein said benzopyrylium salt is 2-phenylbenzopyrylium perchlorate and said benzopyran is 2-(p-methoxystyryl)-3-phenyl-4,6-dimethoxy-1,4-benzopyran.

7. A sensitizer according to claim 2 wherein said benzopyrylium salt is 2-phenylbenzopyrylium perchlorate and said benzopyran is 2-(p-methoxystyryl)-3-phenyl-4-methoxy-6-methyl-1,4-benzopyran.

8. A sensitizer according to claim 2 wherein said benzopyrylium salt is 2-(p-nitrophenyl)benzopyrylium perchlorate and said benzopyran is 2-(p-methoxystyryl)-3-phenyl-4,6-dimethoxy-1,4-benzopyran.

9. A sensitizer according to claim 2 wherein said benzopyrylium salt is 2-(p-chlorophenyl)benzopyrylium perchlorate and said benzopyran is 2-(p-methoxystyryl)-3-phenyl-4,6-dimethoxy-1,4-benzopyran.

10. A sensitizer according to claim 2 wherein said benzopyrylium salt is 2-(p-nitrophenyl)-6-methoxybenzopyrylium perchlorate and said benzopyran is 2-(p-methoxystyryl)-3-phenyl-4,6-dimethoxy-1,4-benzopyran.

11. A sensitizer according to claim 2 wherein said benzopyrylium salt is 2-(D-chlorophenyl)-6-methoxybenzopyrylium perchlorate and said benzopyran is 2-(p-methoxystyryl)-3-phenyl-4,6-dimethoxy-1,4-benzopyran.

12. A sensitizer according to claim 2 wherein said benzopyrylium salt is 2-(p-chlorophenyl)-6-methoxybenzopyrylium perchlorate and said benzopyran is 2-(p-methoxystyryl)-3-phenyl-4-methoxy-6-methyl-1,4-benzopyran.

13. A sensitizer according to claim 2 wherein said benzopyrylium salt is 2-(p-aminophenyl)benzopyrylium perchlorate and said benzopyran is 2-(p-methoxystyryl)-3-phenyl-4,6-dimethoxy-1,4-benzopyran.

14. A sensitizer according to claim 2 wherein said benzopyrylium salt is 2-(p-methylphenyl)benzopyrylium perchlorate and said benzopyran is 2-(p-methoxystyryl)-3-phenyl-4,6-dimethoxy-1,4-benzopyran.

15. A sensitizer according to claim 2 wherein said benzopyrylium salt is 2-(p-methoxyphenyl)benzopyrylium perchlorate and said benzopyran is 2-(p-methoxystyryl)-3-phenyl-4,6-dimethoxy-1,4-benzopyran.

16. A sensitizer according to claim 1 wherein said benzopyrylium salt is 2-p-cyanostyryl-3-phenyl-6-chlorobenzopyrylium perchlorate and said benzopyran is 2-p-methoxyphenyl-4-methoxy-6-methyl-1,4-benzopyran.

17. A sensitizer according to claim 1 wherein said benzopyrylium salt is 2-(2,4-dichlorostyryl)-3-phenyl-6-nitrobenzopyrylium perchlorate and said benzopyran is 2-p-methylphenyl-4-methoxy-6-chloro-1,4-benzopyran.

18. A sensitizer according to claim 1 wherein said benzopyrylium salt is 2-(α-isopropyl-p-carboxystyryl)-6-methylbenzopyrylium perchlorate and said benzopyran is 2-p-chlorophenyl-4,5-dimethoxy-1,4-benzopyran.

19. A sensitizer according to claim 1 wherein said benzopyrylium salt is 2-p-nitrostyryl-3-phenyl-6-nitrobenzopyrylium perchlorate and said benzopyran is 2-p-aminophenyl-4-methoxy-1,4-benzopyran.

20. A sensitizer according to claim 1 wherein said benzopyrylium salt is 2-p-methoxy styryl-3-phenyl-6-chlorobenzopyrylium perchlorate and said benzopyran is 2-p-nitrophenyl-4-methoxy-1,4-benzopyran.

21. A sensitizer according to claim 2 wherein said benzopyrylium salt is 2-phenyl-6-methoxybenzopyrylium perchlorate and said benzopyran is 2-(α-isopropyl-p-carboxystyryl)-4-methoxy-6-methyl-1,4-benzopyran.

22. A sensitizer according to claim 2 wherein said benzopyrylium salt is 2-p-methoxyphenyl-6-methylbenzopyrylium perchlorate and said benzopyran is 2-p-cyanostyryl-3-phenyl-4-methoxy-6-chloro-1,4-benzopyran.

23. A sensitizer according to claim 2 wherein said benzopyrylium salt is 2-phenyl-6-chlorobenzopyrylium perchlorate and said benzopyran is 2-(2,4-dichlorostyryl)-3-phenyl-4-methoxy-6-nitro-1,4-benzopyran.

24. A sensitizer according to claim 2 wherein said benzopyrylium salt is 2-p-nitrophenylbenzopyrylium perchlorate and said benzopyran is 2-p-methylstyryl-3-phenyl-4-methoxy-6-ethyl-1,4-benzopyran.

* * * * *